United States Patent
Matsuno (10) Patent No.: US 7,130,377 B2
(45) Date of Patent: Oct. 31, 2006

(54) X-RAY IMAGE TAKING APPARATUS AND OPERATION CONTROL PROGRAM THEREOF

(75) Inventor: Hiroyuki Matsuno, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/963,013

(22) Filed: Oct. 12, 2004

(65) Prior Publication Data
US 2005/0084068 A1  Apr. 21, 2005

(30) Foreign Application Priority Data
Oct. 17, 2003  (JP)  ............................. 2003-357775

(51) Int. Cl.
*H05G 1/38* (2006.01)
(52) U.S. Cl. ........................... 378/96; 378/62; 378/116
(58) Field of Classification Search .................. 378/62, 378/96, 97, 98.8, 115, 116; 250/370.08, 250/370.09
See application file for complete search history.

(56) References Cited
U.S. PATENT DOCUMENTS
2002/0050568 A1 *  5/2002  Nonaka ................. 250/370.09

FOREIGN PATENT DOCUMENTS
JP     10-208016    8/1998

* cited by examiner

Primary Examiner—Courtney Thomas
(74) Attorney, Agent, or Firm—Morgan&Finnegan LLP (57) ABSTRACT

An X-ray image taking apparatus which takes an X-ray image by using an FPD juxtaposing TFTs performs the return processing of the FPD according to an inputted image taking parameter when the image taking parameter such as exposure time is inputted with an input unit for a long-time image taking operation mode, a high dose image taking operation mode, or the like.

8 Claims, 5 Drawing Sheets

| PATIENT ID | PATIENT NAME | IMAGE TAKEN PART |
|---|---|---|
| | SELECT PATIENT | |
| 0001 | YAMADA TARO | TRUE LATERAL VIEW OF CHEST, ... |
| 0004 | TANAKA HANAKO | FEMUR, ... |
| ...... | ...... | ...... |

X-RAY IMAGE TAKING APPARATUS AND OPERATION CONTROL PROGRAM THEREOF

This application claims priority from Japanese Patent Application No. 2003-357775 filed Oct. 17, 2003, which is hereby incorporated by reference herein.

BACKGROUND OF THE INVENTION

1. Field of the Invention

The present invention relates to an X-ray image taking apparatus which makes modification of an image taking operation mode possible, and an operation control program thereof.

2. Related Background Art

Up to now, a film screen system where an intensifying screen and an X-ray photographic film has been widely used for an X-ray image taking operation aiming at a medical diagnosis. A film image which is given the X-ray image taking operation is hung on a schaukasten and is observed, and the film is designed so as to become in the contrast which is in a tone range of being easy to observe a diagnostic part. Nevertheless, when a image taking parameter shifts, overexposure and underexposure tend to easily arise, and hence, there is a possibility of having an adverse effect on a diagnosis.

It has been started in recent years that an X-ray digital image taking apparatus of adopting an FPD (Flat Panel Detector) as a plane sensor converting an X-ray image into an electrical signal proportional to the strength of X-rays is used. Since extracting a feature of an image with image processing technology, this image taking apparatus can solve a former problem of exposure adjustment and further has a function of enhancing diagnostic ability by image processing such as image enhancement.

When this kind of FPD is used, it is desirable to correct an offset since a noise component caused by a dark current is added to an image as the offset. In general, offset noise (FPN: fixed pattern noise) is expressed as a function of accumulation time of a sensor. As an offset correction method, as described in Japanese Patent Application Laid-Open No. 10-208016, there is a known method of storing a FPN image, corresponding to accumulation time inputted into the FPD, in memory and performing correction by subtracting the FPN image from a taken image.

Nevertheless, in the above-mentioned offset correction method, when a special image taking operation such as a long-time image taking operation is performed, a condition of the noise component caused by the dark current changes. Hence, since a device which performs behavior like a defective pixel appears, an image processing condition changes in automatic exposure adjustment. Therefore, since a correction error arises, manual adjustment becomes necessary, or there is a possibility of affecting a diagnosis.

Then, a method of changing the correction method by inputting an operating temperature change and operation time of FPD into a correction circuit is also known. Nevertheless, since this is implemented by hardware so as to be processed in real time, there is a problem of becoming expensive.

SUMMARY OF THE INVENTION

The present invention aims at providing an X-ray image taking apparatus, which decreases noise by changing an operating method of a two-dimensional sensor according to a image taking parameter, and an operation control program thereof. In order to achieve the above object, for example, a radioactive ray image processing apparatus of the present invention comprises the following arrangement.

That is, a radioactive ray image processing apparatus which reconfigurates a CT image from a plurality of image data obtained by image taking an examined object in different angles comprises:

body motion information extraction means which extracts information based on an examined object from at least two image data and calculates a fluctuation amount, showing a body motion of the above-mentioned examined object, on the basis of the information; and CT reconstruction means reconfigurating a CT image from the plurality of above-mentioned image data, wherein re-image taking operation judgment means judges the necessity of re-image taking operation from at least one of the above-mentioned fluctuation amounts and the above-mentioned CT reconfiguration means starts reconfiguration when there is no need for the re-image taking operation.

In order to achieve the above object, for example, an X-ray image taking apparatus of the present invention comprises the following arrangement.

That is an X-ray image taking apparatus comprising:

radioactive ray generation means of generating a radioactive ray;

a two-dimensional sensor which converts the above-mentioned radioactive ray into an electrical signal by using a juxtaposed photoelectric transducer;

control means which controls the operation of the above-mentioned radioactive ray generation means and the above-mentioned two-dimensional sensor, wherein the above-mentioned control means changes the operating methods of the above-mentioned two-dimensional sensor before and after an image taking operation according to control parameters of the above-mentioned radioactive ray generation means.

In order to achieve the above object, for example, an operation control program of the present invention comprises the following arrangement.

That is, an X-ray image taking apparatus which takes an X-ray image by using a two-dimensional sensor which is juxtaposed with a photoelectric transducer, making a computer execute:

a step of indicating an image taking parameter with an image taking operation database in order to control an image preparing operation;

a step of acquiring an operating parameter from the above-mentioned image taking operation database according to the indicated image taking parameter; and a control step of switching sensor operation control methods according to the above-mentioned driving parameter.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Preferred embodiments of the present invention will now be described in detail in accordance with the accompanying drawings.

Figure 1:
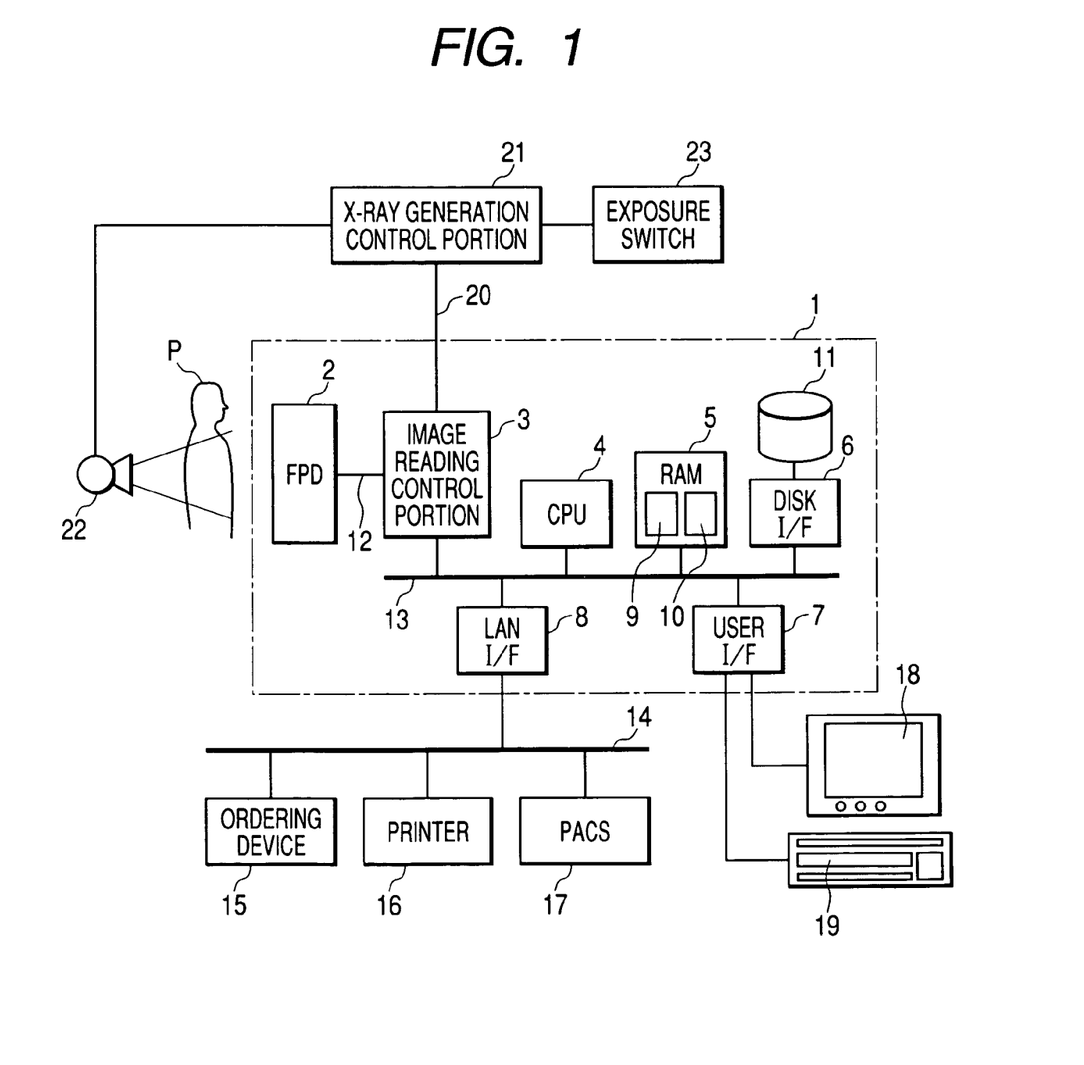
FIG. 1 is a block diagram of an X-ray image taking apparatus.

FIG. 1 shows a block diagram of this embodiment. A medical-application X-ray image taking apparatus 1 comprises an FPD 2 which is a two-dimensional sensor which uses TFTs (thin-film transistor(s)) and has a fluorescent substance and a big screen photoelectric transducer, an image reading control portion 3 storing an image, a CPU 4, RAM 5 storing a control program, a disk interface 6, a user interface 7 communicating with an operator, and a LAN interface 8 for communicating with an external device. In the RAM 5, RAM 10 temporarily containing a system control program 9 and a taken image is provided. In addition, a hard disk 11 which stores a taken image, a control program 9, correction information, etc. is connected to the disk interface 6.

In addition, the FPD 2 and image reading control portion 3 are connected through a data line 12 for power, image transfer, and a control signal. Further, the image taking operation control portion 3, CPU 4, RAM 5, disk interface 6, user interface 7, and LAN interface 8 are connected mutually with an internal bus 13.

Furthermore, the LAN interface 8 is connected through the LAN 14 to an ordering device 15 receiving an image taking operation order from the outside, and a printer 16 and a PACS 17 which are external devices outputting a taken image so as to present the taken image for a diagnosis. Moreover, a display unit 18 and an input unit 19 such as a keyboard and a mouse are connected to the user interface 7. Of course, the display unit 18 and input unit 19 may be also touch-sensitive.

The image reading control portion 3 is connected to an external X-ray generation control portion 21 through a synchronizing signal line 20, and this X-ray generation control portion 21 is connected to an X-ray tube 22 and an exposure switch 23.

At the time of an image taking operation, the CPU 4 of the X-ray image taking apparatus 1 first receives ordering information, outputted from a radiology information system (RIS) which is not shown, from the ordering device 15.

Figure 2:
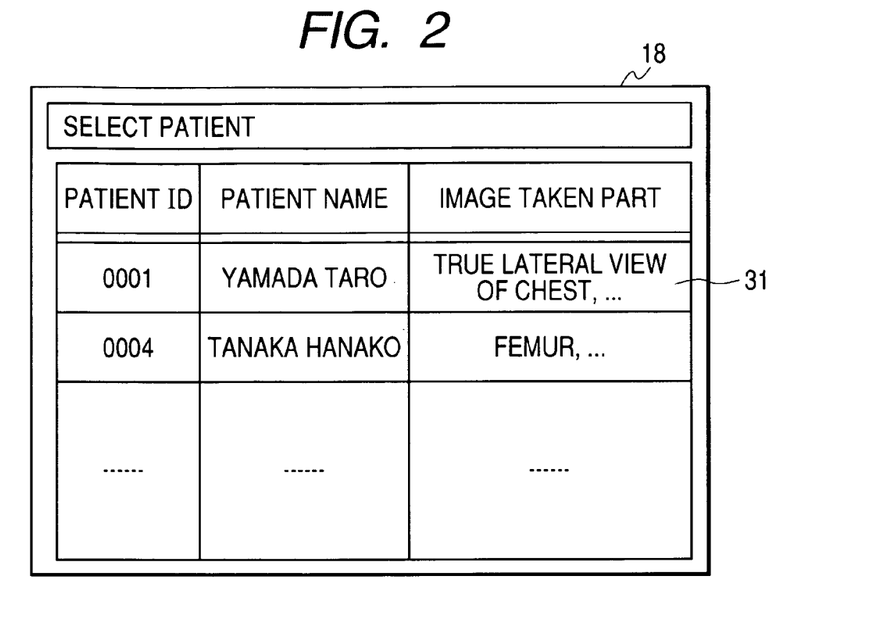
FIG. 2 is a front view of a display unit.
Figure 3:
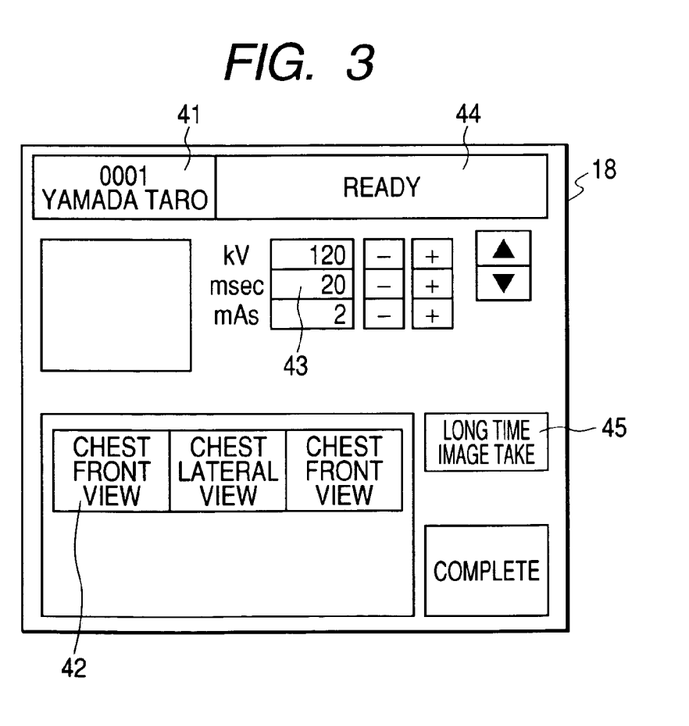
FIG. 3 is a front view of the display unit.

FIG. 2 shows a screen of the display unit 18, and displays a list of a patient ID, a patient name, and an image taken part to display a list of ordering information which is received from the ordering device 15. When a radiological technician who is an operator of the X-ray image taking apparatus 1 inputs an examination item displayed on a display portion 31 of the display unit 18 through the input unit 19, detailed image taking operation order data as shown in FIG. 3 is displayed on a screen of the display unit 18.

On the screen of this display unit 18, in order to present the operator the examination item selected in the display portion 31, for example, a patient ID, a name, a date of birth, etc. are displayed on a display portion 41 as patient information. In addition, a display portion 42 which displays an image taking operation order which is constructed of image taken parts which are received from the ordering device 15 is provided. Furthermore, a display portion 43 which displays an image taken parameter of an image taking operation order, a display portion 44 which displays the state of the X-ray image taking apparatus 1, and a long-time image taking operation button 45 are provided.

When the operator clicks an image taking operation order button of the display portion 42, the control program 9 reads an image processing parameter and an image taking parameter suitable for an individual image taking operation method stored in the database in the hard disk 11, and determines them as image taking parameters to be used to use them for image taking operation control. The CPU 4 starts an image taking operation and makes a "chest front view" image taking operation order button, which is a first image taken part of the ordering information shown in the display portion 42, be in a selective state.

The operator locates a patient P, whose image is taken, between the FPD 2 and X-ray tube 22, and arranges him/her in an image taking posture. Meanwhile, the CPU 4 applies a voltage to the FPD 2 by the control program 9, and sends a command of an image preparing operation so that X-ray image taking operation can be performed with the FPD 2. The control program 9 receives the command and makes the FPD 2 shift to the state in which the X-ray image taking operation becomes ready. That is, after standby for several seconds until a noise component generated regardless of light and is called a dark current decreases, when detecting that the FPD 2 is ready for the X-ray image taking operation, the control program 9 displays "READY" on a display portion 44.

In addition, in the X-ray image taking apparatus 1, a heavy dark current flows immediately after a voltage being applied to the photoelectric transducer. That is, it becomes possible to acquire an X-ray image with a small noise component by performing the image taking operation after a dark current decreases with monitoring the elapsed time after applying the voltage. That is, during this time of decreasing the dark current, the apparatus 1 displays in the display portion 44 that the apparatus 1 is in the ready state as mentioned above.

Then, an FPN image of fixed pattern noise of the FPD 2 is acquired after X-ray irradiation, the FPN image is subtracted from the acquired X-ray image, and an X-rays taken image except the influence of the FPN is acquired.

In addition, in the FPD 2 which uses TFTs like this embodiment, since the lifetime of the TFTs is determined by the time when a voltage is applied, it deteriorates transfer capability to keep the TFTs on. Since a phenomenon of sensitivity decrease of the FPD 2 is caused as a result, an operating method which makes the on-time of the TFTs as short as possible is desirable.

Figure 4:
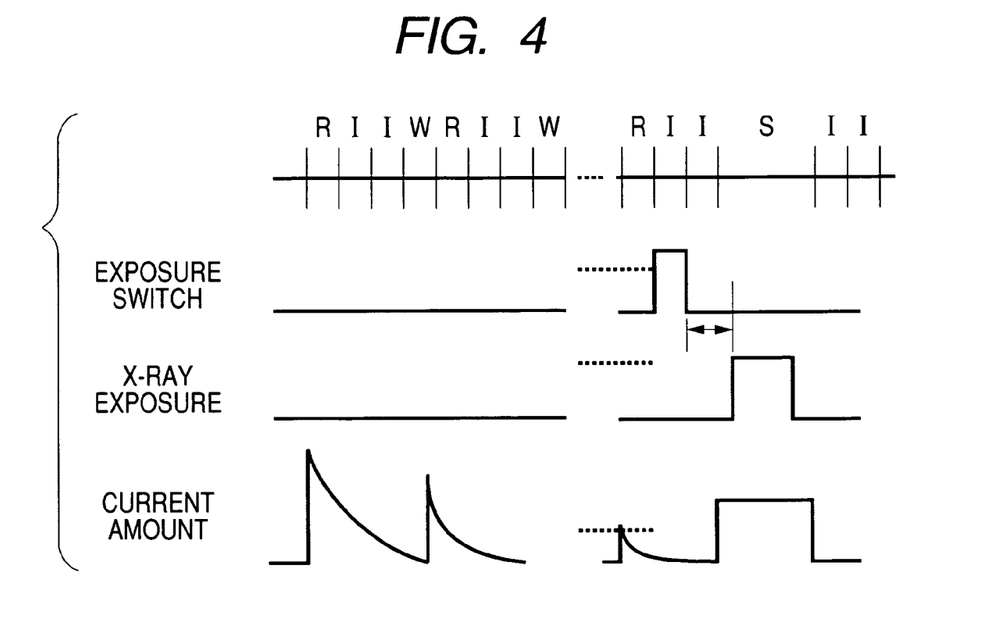
FIG. 4 is an operation timing-chart showing a short-time image preparing operation.

For example, at the time of the operation timing-chart as shown in FIG. 4, after one refresh operation (R) of discharging electric charges accumulated in the FPD 2 until the dark current became small, and two initializing operations (I) of performing the ON/OFF of the TFTs so as to discharge the dark current are performed, one standby operation (W) of maintaining the TFTs off is performed. Then, since an operation frequency of the TFTs decreases in comparison with the case that the standby operation (W) is not performed, this contributes to the improvement in the lifetime, i.e., reliability of the FPD 2. In this way, when a preparing operation for decreasing the dark current is repeatedly performed and suitable time elapses, it is judged that the amount of the dark current becomes suitable for the image taking operation, and hence, as mentioned above, it is displayed for the operator in the display portion 44 that the FPD 2 is ready for the image taking operation.

In this embodiment, for example, in the case of a normal short-time image taking operation for 5 ms to 1000 ms, preparing operation time until the FPD 2 becomes in the above-described ready state for a image taking operation is defined as 10 seconds. For these 10 seconds, as mentioned above, by repeating the refresh operation (R), initializing operation (I), and standby operation (W), the dark current is discharged and the image taking operation is waited.

The operator depresses the exposure switch 23, after confirming that the FPD 2 is in the ready state for an image taking operation in the display portion 44 of the display unit 18, to input into the system a trigger for generating X-rays. An exposure signal generated by depressing this exposure switch 23 is inputted into the image reading control portion 3 through the synchronizing signal line 20. Then, this image reading control portion 3 starts an accumulation operation (S) in response to the operation timing of the FPD 2 in the state of the control signal, and at the same time, generates an exposure-enabling signal through the synchronizing signal line 20. This exposure-enabling signal is returned to the X-ray generation control portion 21, and the X-ray generation control portion 21 generates X-rays from the X-ray tube 22.

Figure 5:
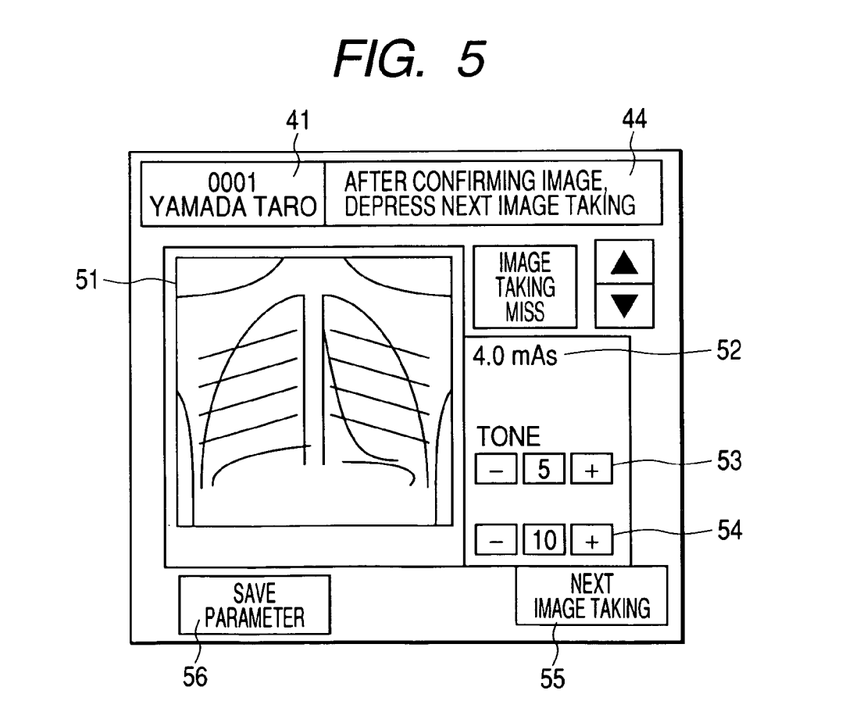
FIG. 5 is a front view of the display unit.

An X-ray image transmitting the Patient P is acquired as digital data in the FPD 2 through the fluorescent substance, and is transferred to the image reading control portion 3. The CPU 4 executes the control program 9, makes the screen of the display unit 18 display the X-ray image through the user interface 7 as shown in FIG. 5, and processing the taken image by using the image processing parameter determined before the image taking operation.

The CPU 4 not only displays the image data acquired from the image reading control portion 3 in a display portion 51 of the display unit 18 and the X-rays generating parameter in a display portion 52, but also saves them into the hard disk 11 through the disk interface 6. In addition, a tone adjust parameter can be set in a display portion 53, and a contrast adjust parameter can be set in a display portion 54. Furthermore, a next image taking button 55 and a save-parameter button 56 for saving a parameter are provided on the screen.

Then, the CPU 4 executes an image analysis by the control program 9, and analyzes the tone of the image automatically. When there is a problem in the automatic tone control of the image displayed on the display portion 51, the operator can change the tone and contrast of the taken image by adjusting the parameters of the display portions 53 and 54.

Subsequently, by the operator clicking the next image taking button 55 for the next image taking operation after finishing the confirmation of the taken image on the screen shown in FIG. 5, the screen returns to the screen shown in FIG. 3, and the user interface 7 selects the next taken part to be requested.

When a long-time image taking operation is performed, for example, in the case of a well-built patient, a normal amount of X-rays may be inadequate in a transit dose and a sufficient taken image for a diagnosis may be unacquirable. In such a case, a device such as a phototimer which monitors the transit dose and stops X-ray irradiation may be used, or exposure time which is longer than the normal time, for example, 1200 ms may be set beforehand. When performing the long-time image taking operation, the long-time image taking operation button 45 is clicked at the time of the amount change of X-rays.

In addition, also when image taking a functional image where the state of performing breath in an image taking operation is taken like respiratory kymography, for example, the long-time image taking operation method for 3000 ms is used. As for the setting of this long-time image taking operation, by increasing X-rays irradiation time setting among the image taking parameters displayed in the display portion 43, or by clicking a long time instruction button not shown, the generation time of X-rays is lengthened to the X-ray tube 22, and according to it, the control program 9 performs the setting of the accumulation time of the FPD 2.

However, when the long-time image taking operation is performed, while the accumulation time becomes long, an output is not stabilized like a defective pixel, the FPN correction does not function correctly, and hence, a pixel which generates a correction error appears. It is known that, in the case of such a long-time image taking operation exceeding 1000 ms, when the preparing operation for 30 seconds is performed as standby time to the ready state, the dark current decreases in comparison with that in the preparing operation for 10 seconds, and hence, an effective output value of the FPD 2 increases or is stabilized.

Figure 6:
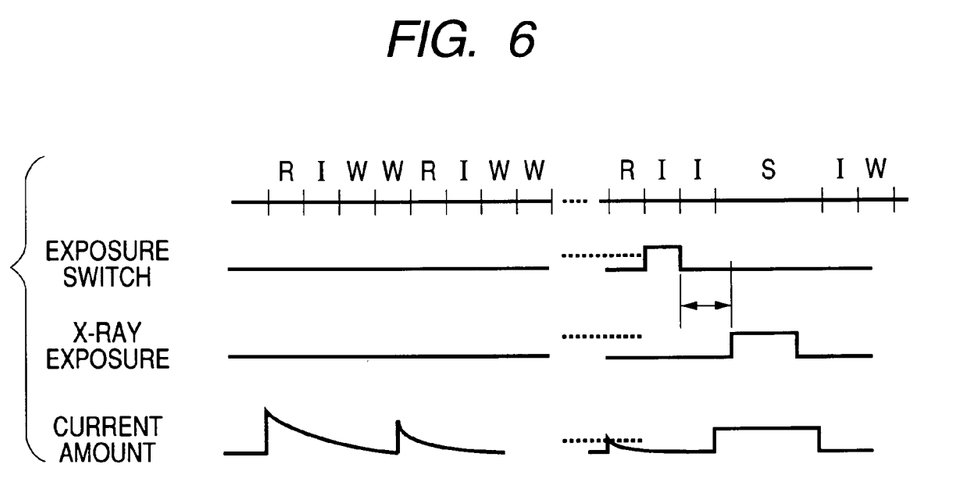
FIG. 6 is an operation timing chart showing a long-time image preparing operation.

However, when an operation timing-chart as shown in FIG. 6 is adopted in order not to degrade the TFTs in vain as mentioned above, it is possible to lessen the dark current to an extent similar to the case that the frequency of the standby operations (W) is 2, and the time of the preparing operation is 30 seconds.

In addition, when a high dose image taking operation is performed, large difference between a passing-through portion, formed by X-rays directly reaching the FPD 2, and an image portion formed by X-rays transmitting the patient P and reaching arises in the accumulated dose of electric charges. In such a case, since electric charges saturating the capacity of the FPD 2 are accumulated in the passing-through portion, an adverse effect that an afterimage appears in the next taken image since the normal refresh operation (R) cannot fully discharges the electric charges may come out. In addition, whether the output of the FPD 2 is saturated is discriminated by a method of comparing whether a pixel value exceeds a threshold value, set beforehand, at the time of implementation of the tone analysis of a taken image.

In this way, when it is detected that the FPD 2 performed the long-time image taking operation or high dose image taking operation, the return processing of the FPD 2 is executed. For example, when the above-mentioned high dose or long-time image taking operation was performed, it is detectable by accumulation time that the long-time image taking operation was performed, and the high dose image taking operation is detectable through image analysis means.

They are detected by the operation of the control program 9, and when it determines that return processing is necessary, an operation for returning the FPD 2 is performed. As for the return operation, for example, a voltage to the TFTs is once turned off for 1 to 3 seconds, and after the voltage is applied again, the refresh operation (R), initializing operation (I), and standby operation (W) are repeated. According to the next exposure time, the apparatus is controlled so that the apparatus may be made to be in the image take preparing operation mode until the dark current decreases, and after that, the apparatus may be made to be in the ready state for an image taking operation.

The operator repeats image taking process similar to the above-mentioned process until all the image taking operation orders are completed. Since the next image taking operation does not exist when all the image taking operations are completed, the CPU 4 displays "examination completion" in the display of the next image taking button 44. Then, when the operator clicks this examination completion button 44, the examination of the patient P can be ended.

When the examination is ended, the control program 9 transmits the image taking parameter and image taking operation information, which are stored in the hard disk 11, to the ordering device 15. According to a communication protocol determined beforehand, the control program 9 transmits the end of the image taking operation for the examination to the ordering device 15.

In addition, according to the standard communication protocol for medical applications which is called DICOM, the control program 9 outputs image data, consisting of the taken image and supplementary information such as the above-described image taking parameter and image taking operation information, to an external device in a lump. The image taking technician leaves the digital X-ray image taking apparatus 1 so as to confirm the taken image, and performs the confirmation of the diagnostic image and the outputted film with the display unit 18. Then, a medical practitioner uses the image for a diagnosis.

Subsequently, when the next patient's examination is started, the FPD 2 is made to be ready for an image take preparing operation. Nevertheless, usually, there is the waiting time for the next image take preparing operation, or the next patient may not have arrived. Then, when an examination is ended, the control program 9 once turns off the voltage of the FPD 2 to make the reliability of the FPD 2 not degraded.

Figure 7:
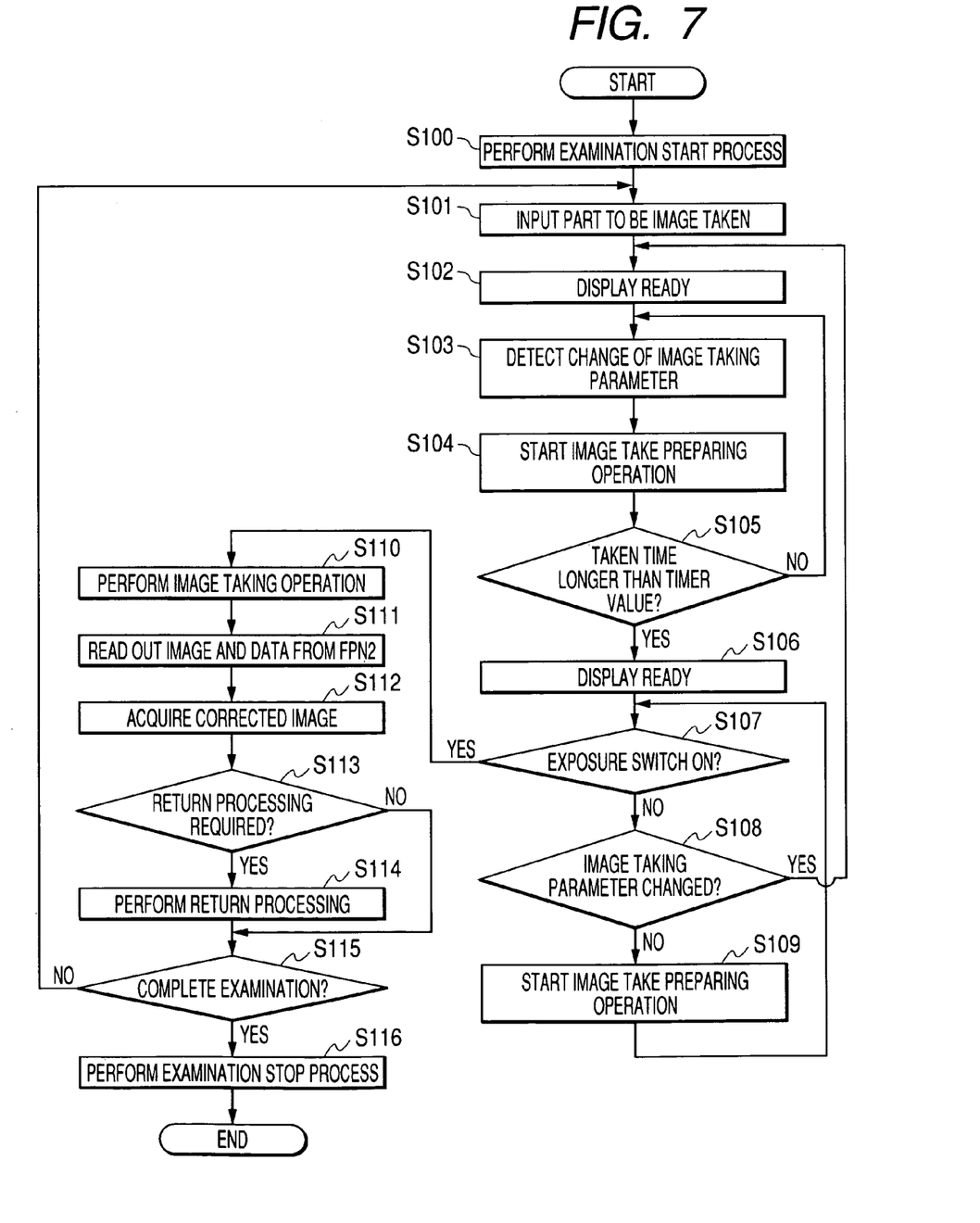
FIG. 7 is a flowchart of a image taking procedure.

FIG. 7 is a flowchart of an image taking procedure, and a method of changing an operating method of the FPD 2 will be explained when an operator changes the image taking parameter set beforehand. First, the operator clicks a button, which shows a taken part, in the display portion 31 of the display unit 18 shown in FIG. 2, and then, the operator changes a dose according to a patient's physique. In this case, when a dose exceeds a threshold value set beforehand, the apparatus is controlled so as to switch the operation method to the operating method of decreasing the dark current of the FPD 2.

Then, when the operator indicates an examination start, patient data and an image taking operation order are acquired from the ordering device 15 at step S100, and are displayed on the screen of the display unit 18. Next, the process goes to step S101. When the operator clicks a button, which shows the taken part, in the display portion 31 according to the image taking operation order, an image taking parameter and an image processing parameter are acquired from the database, which contains a photographing parameter, with a control program 9, and are saved in RAM 5. In order to make the FPD 2 be in the ready state, the process goes to step S102, and "READY" is displayed on the display portion 44.

Subsequently, an input value of the image taking parameter is confirmed at step S103, and the image take preparing operation is started at step S104. For example, when performing the image taking operation for 700 ms in an image taking operation of an abdominal part, as shown in FIG. 4, the refresh operation (R), initializing operation (I), and standby operation (W) are performed as a preparing operation.

Next, at step S105, elapsed time is compared with a timer value set beforehand. When the time is less than this timer value, the process returns to step S103 so as to repeat the above-described preparing operation. When the time spent in the preparing operation becomes longer than the timer value, the process goes to step S106 assuming that the dark current is fully decreased, and "READY" which means the image taking operation is ready is displayed in the display portion 44.

Then, the process goes to step S107, and it is judged whether the exposure switch 23 is depressed. When the exposure switch 23 is depressed, the process goes to step S110 and an image taking operation is performed. Nevertheless, when not depressed, the process goes to step S108 and it is judged whether the operator has changed an image taking parameter.

When there is no modification of the image taking parameter, the process goes to step S109 and the preparing operation is performed. Then, the process returns to step S107, and the preparing operation is again repeated until the exposure switch 23 is depressed. When the modification of the image taking parameter is detected at step S108, the process returns to step S102, and the purport of "in preparation" is displayed and the image take preparing operation is performed again.

For example, when the operator changes exposure time at 1200 ms in order to perform a long-time image taking operation, the value is compared with the threshold value of 1000 ms at step S103. Then, in order to perform the preparing operation for 30 seconds for the long-time image taking operation, the timer value and operating parameter in the RAM 5 are rewritten according to the changed parameters. In the preparing operation at step S104, as shown in FIG. 6, an operating method is changed as the refresh operation (R), initializing operation (I), standby operation (W), and standby operation (W), and the apparatus is controlled to repeat the preparing operation until the timer expires. After that, as described above, it is discriminated whether the exposure switch 23 is depressed, and the image take preparing operation is repeated until the exposure switch 23 or image taking parameter on the screen is changed. The depressing of the exposure switch 23 is detected at step S107, and the process goes to step S110.

Optimal operating parameters are used at the above program steps, and at step S110, the operation for an image taking operation, for example, the refresh operation (R) and initializing operation (I) are performed. At step S111, the X-ray image and data from the FPN 2 are read with being synchronized with X-ray irradiation timing, and thereafter, a corrected image is acquired at step S112. Subsequently, at step S113, the image data for judging whether the above-described return operation is necessary is analyzed, and, for example, when a maximum pixel value is larger than a threshold value set beforehand, it is judged that return processing is necessary since the high dose image taking operation was performed. Then, the return processing is executed at step S114.

When the return processing is not needed, the process goes to step S115, and it is judged whether the image taking operations of the examination order are ended. When all the image taking operations are ended, the process goes to step S116, and power is turned off. When the examination order is not ended, the process returns to step S101, and the above-described steps are repeated for the image taking operations until all the image taking operations are ended. The control of the sensor according to exposure time is achieved by the above steps. When a long-time image taking operation was performed, the apparatus is controlled to execute return processing.

According to the X-ray image taking apparatus and its operation control program of the invention, the quality of an image at the time of an image taking operation is adjusted by performing the optimal operation of the sensor by changing return processing conditions corresponding to an image taking operation mode. Hence, it is possible to elongate the lifetime of the sensor.

In addition, by not only omitting the preparation of a photographing parameter database separately for a special image taking operation such as a long-time image taking operation, but also decreasing an operation frequency of the sensor, it is possible to elongate the lifetime of the sensor.

Furthermore, since the return processing of the sensor is executed according to an image taking parameter or an image analysis of a taken image, it is possible to reduce the influence to the subsequent taken image.

Although the case that the control program 9 stored in a hard disk is transferred to the RAM 5 and is executed by the CPU 4 is explained in the embodiment, the present invention is not restricted to this embodiment. The control program 9 may be implemented by using an arbitrary storage medium, or can be implemented by a circuit which performs the same operation. In addition, the embodiment may be applies to a system which comprises a plurality of devices, or may be applied to a device which consists of one instrument.

In addition, it is not necessary to say that it is also possible to attain the functions of this embodiment by supplying a recording medium, where the program code of the software which achieves the functions of this embodiment is recorded, to a system or a device, and a computer or a CPU of the system or device reading and executing the program code which is stored in the recording medium. In this case, since the program code itself read from the recording-medium achieves the functions of the above-mentioned embodiment, the recording medium recording the program code constructs the present invention.

What are used as the recording media for supplying the program code are, for example, a floppy disk, a hard disk, an optical disk, a magneto-optical disk, CD-ROM, CD-R, a magnetic tape, a non-volatile memory card, and ROM.

In addition, not only the functions of the embodiment mentioned above are achieved by executing the program code which the computer reads, but also it is possible to achieve the functions of the above-mentioned embodiment by a part or all of processing being executed by an OS or the like, which is working on the computer, on the basis of instructions of the program code.

Furthermore, it is also possible to achieve the functions of the above-mentioned embodiment by writing the program code, read from the recording medium, in memory provided in a feature expansion board inserted in a computer, or a feature expansion unit connected to a computer, and thereafter, a part or all of actual processing being executed by a CPU or the like, which is provided in the feature expansion board or feature expansion unit, on the basis of instructions of the program code.

In addition, the present invention is also applicable to the case that a program is distributed to a requiring person from a storage medium, recording the program code of the software achieving the functions of the above-mentioned embodiment, via a communication line such as the Internet.

As described above, the present invention can provide an X-ray image taking apparatus, which decreases noise by changing an operating method of a two-dimensional sensor according to an image taking parameter, and an operation control program thereof.

As many apparently widely different embodiments of the present invention can be made without departing from the spirit and scope thereof, it is to be understood that the invention is not limited to the specific embodiments thereof except as defined in the claims.

What is claimed is:

1. An X-ray image taking apparatus comprising:
    a two-dimensional sensor which converts a radiation ray into an electrical signal by using a photoelectric transducer; and
    a control means which controls combination of (1) a refresh operation of discharging accumulated electric charges of the photoelectric transducer, (2) an initializing operation of turning on/off electricity to the photoelectric transducer, and (3) a standby operation of maintaining the cutting off electricity to the photoelectric transducer, and operation times thereof,
    wherein the control means changes the combination of (1) the refresh operation, (2) the initializing operation, and (3) the standby operation, and the operation times thereof in accordance with an exposure time or a transit dose of the radiation ray.

2. An X-ray image taking apparatus according to claim 1, wherein the control means elongates the time of(3) the standby operation with an elongation of the exposure time.

3. An X-ray image taking apparatus according to claim 1, wherein the control means changes combination of (1) the refresh operation, (2) the initializing operation, and (3) the standby operation and the operation times thereof, after performing a long-time image taking operation or the a high dose image taking operation.

4. An X-ray image taking apparatus according to claim 1, wherein the control means elongates the time of (3) the standby operation more than a time of a normal image taking operation, after performing the a long-time image taking operation or a high dose image taking operation.

5. An X-ray image taking apparatus according to claim 1, wherein the control means changes the combination of the three operations (1) the refresh operation, (2) the initializing operation, and (3) the standby operation, and the operation times thereof, on the basis of values of the image data obtained at a high dose image taking operation.

6. An X-ray image taking apparatus according to claim 1, wherein the control means eliminates a residual image of the two-dimensional sensor, by maintaining (3) the standby operation for at least 1 second, and thereafter, restarting (1) the refresh operation, after performing a long-time image taking operation or a high dose image taking operation.

7. An X-ray image taking apparatus which takes an X-ray image by using a two-dimensional sensor which is with a photoelectric transducer, said apparatus having a processor programmed to control of the X-ray image taking apparatus to execute the steps of:
    converting a radiation ray into an electrical signal by using a two-dimensional sensor having a photoelectric transducer; and
    controlling a combination of (1) a refresh operation of discharging accumulated electric charges of the photoelectric transducer, (2) an initializing operation of turning on/off electricity to the photoelectric transducer, and (3) a standby operation of maintaining the cutting off electricity to the photoelectric transducer, and operation times thereof in accordance with an exposure time or a transit dose of the radiation ray.

8. A method for taking X-ray images comprising:
    converting a radiation ray into an electrical signal by using a two-dimensional sensor having a photoelectric transducer; and
    controlling a combination of (1) a refresh operation of discharging accumulated electric charges of the photoelectric transducer, (2) an initializing operation of turning on/off electricity to the photoelectric transducer, and (3) a standby operation of maintaining the cutting off electricity to the photoelectric transducer, and operation times thereof, in accordance with an exposure time or a transit dose of the radiation ray.

* * * * *